US005175368A

United States Patent [19]

[11] Patent Number: 5,175,368

Tafesh et al.

[45] Date of Patent: Dec. 29, 1992

[54] PROCESS FOR THE PREPARATION OF ARYLALKYLAMINES AND SUBSTITUTED ARYLALKYLAMINES

[75] Inventors: Ahmed M. Tafesh; Joseph A. McDonough; Graham N. Mott, all of Corpus Christi, Tex.

[73] Assignee: Hoechst Celanese Corporation, Somerville, N.J.

[21] Appl. No.: 908,587

[22] Filed: Jun. 29, 1992

Related U.S. Application Data

[63] Continuation of Ser. No. 630,127, Dec. 19, 1990, abandoned.

[51] Int. Cl.[5] C07C 209/52

[52] U.S. Cl. 564/375; 562/59; 562/66; 562/125; 564/374; 564/378; 564/382

[58] Field of Search 564/375, 374, 378, 382; 562/59, 66, 125

[56] References Cited

U.S. PATENT DOCUMENTS

| | | | |
|---|---|---|---|
| 1,995,709 | 3/1935 | Hartung | 564/358 |
| 2,505,645 | 4/1950 | McPhee | 564/358 |
| 2,567,906 | 9/1951 | Hartung | 564/358 |
| 2,784,228 | 3/1957 | Hartung | 564/358 |
| 3,028,429 | 4/1962 | Wilbert et al. | 564/358 |
| 3,929,871 | 12/1975 | Carlsson et al. | 564/375 |
| 3,966,813 | 6/1976 | Satzinger et al. | 564/358 |
| 4,169,108 | 9/1979 | Bailey | 564/378 |

OTHER PUBLICATIONS

"Isolation and Synthesis of p-Hydroxyphenylethylamine, an Active Principle of Ergot Soluble in Water", G. Barger, J. Chem. Soc., vol. 95, p. 1127, (1909).

"Reduction of Hydroxymandelonitriles. A New Synthesis of Tyramine", Johannes S. Buck, J. Am. Chem. Soc., vol. 55, p. 3389, (1933).

"Production of Amines by Nitrate Reducing-Bacteria and Lactobacilli for Sake-Brewing", Hakkokogaku Kaisha vol. 55(2), pp. 68-74, (1977).

Hartung and Simonoff, *Org. React.* 7, 263, 326 (1953).

Klabunovskii, *Russ. Chem. Rev.* 35, 546, 558 (1966).

Rylander, "Catalytic Hydrogenation over Platinum Metals," pp. 449-468; Academic Press, Inc., N.Y. 1967.

March, *Advanced Organic Chemistry*, 2nd Ed., p. 402 (1977).

*Primary Examiner*—Richard L. Raymond
*Assistant Examiner*—Scott C. Rand
*Attorney, Agent, or Firm*—Donald R. Cassady; J. Rosenstock

[57] ABSTRACT

Arylalkylamines (as the hydrochloride salt), e.g. tyramine hydrochloride, are prepared by hydrogenating substituted or unsubstituted aryl-α-oximinoalkyl ketones, e.g. p-hydroxyisonitroacetophenone, in either in an aqueous reaction medium comprising hydrochloric acid, essentially without the presence of a lower alkyl alcohol in said reaction medium, or in an aqueous reaction medium comprising water, hydrochloric acid, and a lower alkyl alcohol, wherein the alcohol comprises less than about 90% by volume of the reaction medium. A substituent on the aryl portion of the aryl-α-oximinoalkyl ketone must be on a position which activates the aromatic ring.

39 Claims, No Drawings

PROCESS FOR THE PREPARATION OF ARYLALKYLAMINES AND SUBSTITUTED ARYLALKYLAMINES

This is a continuation of application Ser. No. 07/630,127, filed Dec. 19, 1990, now abandoned.

BACKGROUND OF THE INVENTION

This invention pertains particularly to a process for the preparation of substituted or unsubstituted arylalkylamines from substituted or unsubstituted aryl-α-oximinoalkyl ketones by hydrogenation reduction of the oximino group to an amine and dehydroxylation of an hydroxyl group produced by hydrogenation reduction of the keto group.

Substituted and unsubstituted arylalkylamines are chemical intermediates of great importance. They are used in the preparation of pharmacologically active compounds and in some instances are themselves pharmacologically active. For example, phenethylamine and hydroxyphenethylamine (tyramine) have sympathomimetic (adrenergic) action. Tyramine also is a moiety in opiates, and is useful as an intermediate or substituent in the preparation of other physiologically active compounds or compositions. Hydroxyltyramine (dopamine) is a physiologically important neural inhibitory transmitter.

A common aspect of historic methods of preparing arylalkylamino alcohol dehydroxylation precursors of arylalkylamines is use of lower alkyl alcohols as reaction mediums for catalytic hydrogenation of aryl-α-oximinoalkyl ketones. In U.S. Pat. Nos. 1,995,709 and 2,567,906 by Hartung, a multi-operations procedure for the preparation of substituted phenyl propanol amines is described, particularly, for 1-(p- or m-hydroxyphenyl)-2-amino-1-propanol (in U.S. Pat. No. 1,995,709), and 1-(p-aminophenyl)-2-amino-1-propanol (in U.S. Pat. No. 2,567,906). In U.S. Pat. No. 1,995,709, p- or m-hydroxypropiophenone is reacted with a lower alkyl nitrite in ether in the presence of hydrogen chloride to produce p- or m-hydroxyisonitrosopropiophenone, which then is separated from the reaction mixture by alkaline extraction and recovered from the alkaline solution by precipitation induced by acidification of the extract, after which the precipitate is recrystallized. The p- or m-hydroxyisonitrosopropiophenone thus separated is then reacted with hydrogen in the presence of palladium on charcoal in absolute alcohol containing dry hydrogen chloride until reduction stops, after which the amino ketone is recovered as a filtrate. The filtrate is dryed and purified by recrystallization. Then the amino ketone is dissolved in water and reacted with hydrogen in the presence of palladium on charcoal. The reaction product is recovered as the hydrochloride of the amino alcohol, for example, the hydrochloride of 1-(p-hydroxyphenyl)-2-aminopropanol (in U.S. Pat. No. 1,995,709and the hydrochloride of 1-(p-aminophenyl)-2-aminopropanol (in U.S. Pat. No. 2,567,906).

In U.S. Pat. No. 2,505,645 by McPhee, the acidic catalytic hydrogenation process described by Hartung is employed in a method of preparing α-phenyl-β-hydroxyphenyl-β-hydroxyethylamine.

U.S. Pat. No. 2,784,228 by Hartung describes a partially aqueous alternative process for the catalytic reduction of aryl-α-oximino alkyls, using alkaline solutions instead of acidic solutions to obtain a desired amino alcohol. Difficulties and shortcomings of the acidic catalytic reduction process described by Hartung in U.S. Pat. Nos. 1,995,709 and 2,567,906 are detailed by Hartung in U.S. Pat. No. 2,784,228 and also by Wilbert et al. in U.S. Pat. No. 3,028,429. In U.S. Pat. No. 3,028,429, Wilbert et al. describe a process for the hydrogenation of isonitrosopropiophenone to produce 1-phenyl-2-aminopropanol which is a modification said to improve yields respecting the general process described by Hartung in U.S. Pat. Nos. 1,995,709 and 2,567,906.

In U.S. Pat. No. 3,966,813 to Satzinger et al. hydroxyacetophenone is reacted with a lower alkyl nitrite in a dipolar aprotic solvent in the presence of a hydrogen chloride catalyst to form m-or p-hydroxyisonitrosoacetophenone. The reaction mixture containing the isonitroso compound is poured into ice water and extracted with ethyl acetate. The ethyl acetate solution is dried, cleaned with charcoal, filtered, and vacuum distilled to recover the compound. After recrystallization, the compound is then catalytically hydrogenated to reduce the isonitroso and keto moieties of the hydroxyisonitrosoacetophenone to form (according to the patent) 1-(m- or p-hydroxyphenyl)-2-amino-1-ethanol. The catalytic hydrogenation disclosed is conducted in an aqueous ethanol solution in the presence of hydrochloric acid in aqueous solution using a palladium on charcoal catalyst.

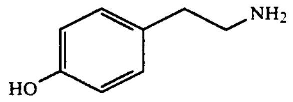

Tyramine (p-hydroxyphenethylamine), is described in the literature as produced by the sodium in ethanol reduction of p-hydroxyphenylmethylcyanate, *J. Chem. Soc.* v.95, p.1127 (1909); by the platinum catalyzed hydrogenation of p-hydroxyphenylmethylcyanate, Buck J. S., *J. Am. Chem Soc.* v.55, p.3389 (1933); and by a lactobacillus decarboxylation of 1-(p-hydroxyphenyl)-2-aminopropionic acid, Umezi, M. et al., *Hakko Kogaku Kaishi*, v.55(2), p.68-74 (1977).

The following U.S. Patents involve various aspects of hydroxyphenethylamine or tyramine but are not as closely related to and do not disclose the process of this invention: U.S. Pat. Nos. 4,885,312; 4,868,218; 4,868,132; 4,861,800; 4,857,522; 4,762,781; 4,699,782; 4,686,179; 4,623,485; 4,609,544; 4,563,263; 4,515,773; 4,503,147; 4,496,655; 4,465,775; 4,436,828; 4,370,495; 4,277,460; 4,207,308; 4,190,593; 4,175,136; 4,032,406; 3,997,608; 3,997,525; 3,993,436; 3,981,982; 3,932,461; 3,894,051; 3,818,015; 3,676,447; 3,576,808; 3,457,354; and 2,695,297.

SUMMARY OF THE INVENTION

In accordance with the present invention, a method for the preparation of the salt of an arylalkylamine is disclosed, the method comprising the steps of:

a compound of the formula

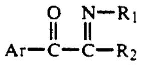

wherein $R_1$ = hydroxyl radical, alkyl, or alkyloxy $R_2$=hydrogen or a $C_1$–$C_8$ alkyl or cycloalkyl, and Ar=an aromatic phenyl unsubstituted, or substituted at the ortho and/or para position; or a naphthyl radical unsubstituted, or substituted at one or more of the 1, 3, 6, and 7 positions; wherein one or more substituents are selected from the group consisting of amino, alkylamino, dialkylamino, hydroxyl, alkoxy, alkyl, phenyl, benzyl, sulfonic acid, and sulfinic acid radicals, wherein alkyl is a branched or unbranched $C_1$–$C_8$ alkyl radical and wherein any alkyl, phenyl and benzyl radicals are optionally substituted with one or more substituents selected from amino, hydroxyl, sulfonic acid, and sulfonic acid radicals, and said phenyl and benzyl substituents are optionally substituted with a $C_1$–$C_8$ alkyl or $C_1$–$C_8$ alkoxy radical, or both;

b) reacting said compound with hydrogen in an aqueous reaction medium comprising hydrochloric acid and a transition metal catalyst to produce a reaction product comprising the salt of an arylalkylamine as its major component.

Typically the conversion of the aryl-α-oximinoalkyl ketones of the formula disclosed above to the salt of an arylalkylamine, using the method of the present invention, results in a yield ranging from about 40% to about 99% based on the aryl-α-oximinoalkyl ketone of the formula provided in step a) above.

The aqueous reaction medium can be an essentially nonalcoholic reaction medium which comprises from about 2% by weight to about 37% by weight hydrochloric acid and a hydrogenation catalyst comprising a transition metal supported on an inert support, wherein the amount of transition metal present ranges from about 0.0005% by weight to about 1.5% by weight based on the amount of the aryl-α-oximinoalkyl ketone compound formula disclosed above.

The aqueous reaction medium can also be one which contains a lower alkyl alcohol. The alcohol is present in quantities of about 90% by volume or less of the aqueous reaction medium. When the lower alkyl alcohol is present, the hydrochloric acid present and the hydrogenation catalyst present can be in the amounts described above for the nonalcoholic reaction medium. When the lower alkyl alcohol is present, a higher concentration of the aryl-α-oximinoalkyl ketone in the reaction medium can be used. For example, a nonalcoholic reaction medium works well with a ketone concentration of about 10% by weight or less based on the reaction medium; a reaction medium comprising about 50% by volume of the lower alkyl alcohol works well with a ketone concentration of about 25% by weight or less based on the reaction medium.

DETAILED DESCRIPTION OF THE INVENTION

As described in the "Background of the Invention", U.S. Pat. No. 3,966,813 to Satzinger et al. claims a process for preparation of 1-(hydroxyphenyl)-2-aminoethanol by reacting a hydroxyacetophenone with a lower alkyl nitrite in a dipolar aprotic solvent in the presence of a hydrogen chloride catalyst to form isonitrosoacetophenone, and then catalytically hydrogenating the isonitrosoacetophenone in the presence of palladium to reduce the isonitroso and keto moieties on the isonitrosoacetophenone molecule. Satzinger et al. provide several examples for the preparation of both m-hydroxyisonitrosoacetophenoneandp-hydroxyisonitrosoacetophenone. However, only one example (Example 4) describes the hydrogenation step for conversion of an hydroxyisonitrosoacetophenone to a 1-(hydroxyphenyl)-2-aminoethanol. Example 4 pertains to hydrogenation of the meta substituted m-hydroxyisonitrosoacetophenone. On the basis of Example 4, Satzinger et al. propose and claim that the para substituted p-hydroxyisonitrosoacetophenone can also be converted by the same hydrogenation step to the aminoethanol.

In accordance with the present invention, it has been discovered that hydrogenation of the p-hydroxyisonitrosoacetophenone does not produce the aminoethanol; instead, p-hydroxyphenethylamine (Tyramine) is produced. The controlling feature appears to be the fact that presence of a hydroxy at the meta position on the hydroxyisonitrosoacetophenone causes a deactivation of the aromatic ring, whereby the benzylic carbon is deactivated toward hydrogenolysis; however, the presence of a hydroxy at the ortho and/or para position activates the aromatic ring, whereby the benzylic carbon is activated toward hydrogenolysis. The deactivated ring affects the hydrogenation reaction so that an aminoethanol is formed. The activated ring affects the hydrogenation reaction so that an ethylamine is formed. Since both para substitution and ortho substitution activate the aromatic ring the ethylamine is formed when a hydroxyl group is present at either or both of these substitution positions.

Further, in accordance with this invention, suprisingly, good yields of substituted and unsubstituted arylalkylamines in the form of hydrochloride salts are obtained by hydrogenating aryl-α-oximinoalkyl ketones, wherein the aryl group is unsubstituted or is substituted at the ortho and/or para position, in the presence of a supported transition metal catalyst in an aqueous reaction medium comprising hydrochloric acid, without use of any significant quantities of a lower alkyl alcohol in the reaction medium, or by hydrogenation of the ketones in a reaction medium comprising a combination of water, hydrochloric acid, and a lower alkyl alcohol, wherein the alcohol comprises less than about 90% by volume of the reaction medium, and wherein the quantity of transition metal catalyst present provides from about 0.0005% by weight to about 5.0% by weight transition metal based on the weight of the aryl-o-oximinoalkyl ketone.

More particularly, the hydrochloride salt of the substituted and unsubstituted arylalkylamines is obtained by reacting about 4 molar equivalents to about 6 molar equivalents of hydrogen based on the quantity of aryl-α-oximinoalkyl ketone, wherein the ketone is present in a quantity ranging from about 5% by weight to about 50% by weight, preferably from about 5% by weight to about 30% by weight, of the reaction medium, and wherein the reaction medium comprises from about 2% by weight to about 37% by weight of hydrochloric acid, and wherein the reaction is carried out in the presence of a transition metal on inert substrate (typically carbon), wherein the overall catalyst composition comprises from about 5% by weight to about 25% by weight, preferably from about 5% by weight to 10% by weight of the transition metal, and wherein the catalyst is present in quantity sufficient to provide from about 0.0005% by weight to about 5.0% by weight, preferably from about 0.001% by weight to about 1.5% by weight, of the transition metal based on weight of the aryl-α-oximinoalkyl ketone. (The reaction medium excludes the aryl-αoximinoalkyl ketone, but includes the transition metal catalyst and the hydrochloric acid.)

When the reaction medium comprises an aqueous solution having a lower alkyl alcohol present, the lower alkyl alcohol comprises less than about 90% by volume of the reaction medium, preferably from about 10% by volume to about 90% by volume of the reaction medium, and more preferable from about 40% by volume to about 70% by volume of the reaction medium, the preferred hydrochloric acid concentration ranges from about 3% by weight to about 30% by weight of the reaction medium, and the preferred concentration of transition metal on inert support catalyst is such that the transition metal provided ranges from about 0.001% by weight to about 1.5% by weight of the aryl-α-oximenoalkyl ketone. Because of the relatively high cost of the palladium catalyst, the discovery that higher yields (85-92% by weight) can be obtained at lower catalyst concentrations than described in the related art makes the process of the present invention more economically feasible. This lower transition metal catalyst concentration is made possible by the higher solubility of the alkyl ammonium salts product and by the increased dielectric constant of the aqueous solution.

When a lower alkyl alcohol is used to form a portion of the aqueous reaction medium, one uses the same quantity in terms of equivalents of hydrogen during the reaction; however, a higher concentration of the aryl-α-oximenoalkyl ketone in the reaction medium is used. For example, a reaction medium comprising about 50% by volume of the alcohol works particularly well with a ketone concentration of about 20% by weight. A reaction medium which contains essentially no alcohol works particularly well with a ketone concentration of about 10% by weight.

The substituted and unsubstituted aryl-α-oximinoalkyl ketone employed in the invention has the formula

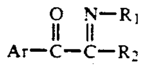

in which $R_1$ represents an hydroxyl group or a $C_1$-$C_8$ alkyl or alkyloxy and $R_2$ represents hydrogen or a $C_1$-$C_8$ alkyl or cycloalkyl, and Ar represents an aromatic phenyl radical unsubstituted, or substituted at the ortho and/or para position, or naphthyl radical unsubstituted or substituted at one or more of the 1, 3, 6, and 7 positions, with one or more substituents selected from the group consisting of amino, alkylamino, dialkylamino, hydroxyl, alkoxy, alkyl, phenyl, benzyl, aryloxy, sulfonic acid, and sulfinic acid radicals, wherein the alkyl in the alkyl-containing substituent(s) is a branched or unbranched $C_1$-$C_8$ alkyl radical and any of such alkyl and the phenyl and benzyl radicals may be optionally substituted with one or more substituents selected from amino, hydroxyl, sulfonic acid, and sulfinic acid radicals, the phenyl and benzyl substituents also or alternatively being optionally substituted with one or more $C_1$-$C_8$ alkyl or $C_1$-$C_8$ alkoxy, or both, radicals.

In a preferred embodiment, tyramine hydrochloride is produced by the method of the present invention using p-hydroxyisonitrosoacetophenone as the aryl-α-oximinoalkyl ketone precusor. When the reaction medium comprises the aqueous solution which does not contain a lower alkyl alcohol, hydrogen is typically reacted with hydrochloric acid in the presence of a palladium on carbon catalyst. The amount of hydrogen reacted ranges from about 4 molar equivalents to about 6 molar equivalents based on moles of p-hydroxyisonitrosoacetophenone. The hydrogen pressure in the reactor preferably ranges from about 15 psig to about 300 psig. The p-hydroxyisonitrosoacetophenone is preferably present in an amount ranging from about 5% by weight to about 50% by weight of the reaction medium, preferably in an amount ranging from about 5% by weight to about 15% by weight of the reaction medium (the reaction medium excludes the p-hydroxyisonitrosoacetophenone, but includes the palladium on carbon catalyst and the hydrochloric acid); the hydrochloric acid is preferably present in the reaction medium in an amount ranging from about 2% by weight to about 37% by weight of the reaction medium; and the palladium on carbon catalyst, which typically comprises about 5% by weight to about 10% by weight palladium, is present in an amount such that the palladium present ranges from about 0.0005% by weight to about 1.5% by weight of the p-hydroxyisonitrosophenone.

When the reaction medium comprises an aqueous solution which comprises a lower alkyl alcohol, hydrogen is reacted with p-hydroxyisonitrosoacetophenone in the presence of hydrochloric acid and in the presence of a palladium on carbon catalyst as previously described. The p-hydroxyisonitrosoacetophenone is present in an amount ranging from about 5% by weight to about 50% by weight of the reaction medium, preferably in an amount ranging from about 10% by weight to about 25% by weight of the reaction medium; and, the hydrochloric acid is preferably present in the reaction medium in an amount ranging from about 3% by weight to about 0% by weight of the reaction medium. The palladium on carbon catalyst, which typically comprises about 5% by weight to about 10% by weight palladium, is preferably present in an amount such that the palladium present ranges from about 0.0005% by Weight to about 1.0% by weight of the p-hydroxyisonitrosoacetophenone. The aryl-α-oximinoalkyl ketone employed for the hydrogenation process of this invention may be prepared by (1) reacting a) an arylalkylketone of the formula

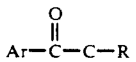

in which R represents hydrogen or a $C_1$-$C_8$ alkyl or cycloalkyl and Ar represents an aromatic phenyl radical unsubstituted, or substituted at the ortho and/or para position, or naphthyl radical unsubstituted or substituted at one or more of the 1, 3, 6, and 7 positions, wherein the substituents, one or more, are selected from the group of amino, alkylamino, dialkylamino, hydroxyl, alkoxy, alkyl, phenyl, benzyl, aryloxy, sulfonic acid, and sulfinic acid radicals, wherein the alkyl in the alkyl-containing substituent(s) is a branched or unbranched $C_1$-$C_8$ alkyl radical and any such alkyl radical as well as the phenyl and benzyl radicals may be optionally substituted with one or more sustituents selected from amino, hydroxyl, sulfonic acid, and sulfinic acid radicals, the phenyl and benzyl substituents also or alternatively being optionally substituted with one or more $C_1$-$C_8$ alkyl or $C_1$-$C_8$ alkoxy, or both, radicals, with b) a lower alkyl nitrite in the presence of hydrogen chloride and in a dipolar aprotic solvent to produce a reaction mixture which includes an aryl-α-oximinoalkyl ketone reaction product; and (2) combining said reaction mixture with water and extracting the aryl-o-oximinoalkyl ketone from the aqueous reaction mixture with an organic solvent selected from lower alkyl esters and lower alkyl alcohols to produce an aryl-α-oximinoalkyl ketone extract solution.

Examples of arylalkylketones usable in the above described process are those wherein the aryl of the arylalkylketone is an unsubstituted phenyl or naphthyl radical or is a substituted phenyl or naphthyl radical having substitution of the kind previously described, such arylalkylketones include, but are not limited to, o- and p-hydroxyacetophenone, o- and p-methylacetophenone, p-ethylacetophenone, p-propylacetophenone, p-butylacetophenone, o-and p-methoxyacetophenone, o- and p-ethoxyacetophenone, 2,4-methoxyacetophenone,p-phenylacetophenone,2-methoxy-4-methylacetophenone, α-acetonaphthone, β-acetonapthone, propiophenone, o- and p-methoxypropiophenone, p-methylpropiophenone, p-ethylpropiophenone, butyrophenone, p-methylbutyrophenone, p-methoxybutyrophenone, valerophenone and p-methylvalerophenone, p-acetamidopropiophenone, p-benzylaminopropiophenone, p-benzoylaminopropiophenone, p-aminoacetophenone, 1-(p-aminophenyl) propiophenone, p-hydroxyphenylacetophenone, p-hydroxyphenylpropiophenone, 1-(4-methylphenyl)propiophenone, and p-phenylsulfonylacetophenone, 4,5 dihydroxy-1-indanone, 5,6-dihydroxy-1-indanone, 4,5 dimethoxy-1-indanone, and 5,6-dimethoxy-1-indanone.

Examples of lower alkyl nitrites usable in the above-described provess for producing the aryl-α-oximinoalkyl ketone include suitable alkyl nitrites are lower alkyl nitrites in which the alkyl radical has from 1 to 8 carbon atoms; including for example, methylnitrite, ethylnitrite, isopropylnitrite, n-butylnitrite, t-butylnitrite, n-hexylnitrite, n-heptylnitrite, n-octylnitrite, and the like.

The dipolar aprotic solvents employed in the nitration of the arylalkylketone are solvents which have a high dielectric constant and a high dipole moment but no acid hydrogen atoms; for example, such solvents include dimethylsulfoxide (DMSO), acetonitrile, dimethylformamide (DMF), dimethylacetamide and hexamethylphosphoric acid triamide (HMPT).

The reaction of the ketone with the lower alkyl nitrite suitably can be carried but at a temperature in the range from −30° C. to 100° C., preferably in the range from 10° C. to 50° C. The amount of hydrogen chloride used suitably is from about 0.5 to 1.2 equivalents, relative to the ketone used. Respecting suitable dipolar aprotic solvents and lower alkyl nitrites and conditions for this aspect of the invention, reference is made to U.S. Pat. No. 3,966,813.

Protic by-products of the dipolar aprotic solvents, for example, amine by-products of DMF, interfer with the efficacy or poison the hydrogenation catalysts employed in this invention. Differential extraction of the reaction mixture containing the aryl-α-oximinoalkyl ketone is essential to remove the amine by-product. The reaction mixture is combined with water, preferably ice, and extracted with multiple volumes of an organic solvent in which the aryl-α-oximinoalkyl ketone is preferentially soluble relative to amines. Suitably the organic solvent is a lower alkyl ester and lower alkyl alcohol, for example, methylacetate, ethylacetate, propylacetate, or ethanol, propanol, or n-butanol.

Hydrogenation of the substituted or unsubstituted aryl-α-oximinoalkyl ketone is carried out using hydrogen in the presence of a transition metal hydrogenation catalyst selected from the group consisting of platinum, palladium, nickel, and rhodium or mixtures thereof on an inert support. The inert support typically comprises carbon or barium sulfate; wherein the hydrogenation catalyst comprises from about 1% by weight to about 25% by weight of the combination including hydrogenation catalyst and inert support. The preferred inert support material is carbon, and the most preferred hydrogenation catalyst comprises palladium on carbon, wherein the palladium comprises from about 5% by weight to about 25% by weight of the combination of palladium on carbon, as previously disclosed. The hydrogenation is conducted under positive hydrogen pressures of from about 15 psig to about 300 psig, preferably in the range from about 45 psig to about 100 psig, at temperatures suitably in the range from about 5° C. to about 100° C., preferably in the range from about 10° C. to about 60° C. At temperatures in the upper part of the useful range, the α-oximinoalkyl ketone conversion to alkylamine proceeds very rapidly and, generally speaking, better reaction control is realized in the preferred temperature range.

The following EXAMPLES illustrate the invention, and are not to be understood as limiting the invention only to these embodiments.

EXAMPLE 1

This example discloses the preparation of tyramine hydrochloride from p-hydroxyphenyl-α-isonitrosoacetophenone in a reaction medium comprising an aqueous solution without the use of a lower alkyl alcohol.

Pure p-hydroxyphenyl-α-isonitrosoacetophenone (11.7g, 70.9 mmol) and 4.3 g of dry 10% by weight palladium on carbon were added to a solution containing 17.8 ml of 37% by volume hydrochloric acid HCl and 100 ml of water (the HCl was about 6.5% by weight of the HCl/water solution). The reactor was sealed and then degassed 3 times with nitrogen, followed by degassing 3 times with hydrogen. The reactor was then pressurized to 50 psi, with hydrogen being added during the reaction to maintain the about 50 psig. The reactor medium was agitated about 1200 rpm. The hydrogen added to the reactor during the reaction was fed into the reactor from a surge vessel; thus, the drop in surge vessel pressure was an indication of hydrogen consumed. The reaction heated itself to 33.4° C., then was heated externally using a heating jacket. The course of the reaction is tabularized below.

| Time (min.) | Temp. (°C.) | Reactor Pressure (psig.) | Surge Vessel (psig) |
|---|---|---|---|
| 0 | 24 | 50 | 592 |
| 30 | 32 | 50 | 548 |
| 45 | 33 | 50 | 529 |
| 75 | 42 | 55 | 505 |
| 105 | 40 | 65 | 484 |
| 135 | 47 | 60 | 476 |
| 165 | 42 | 65 | 476 |
| 220 | 39 | 65 | 476 |
| 250 | 43 | 65 | 463 |

this procedure yielded tyramine hydrochloride in 66% yield based on p-hydroxy-α-isonitrosoacetophenone. The tyramine hydrochloride was isolated by filtering off the catalyst then concentrating the reaction solution in vacuo until crystals formed.

EXAMPLE 2

This example discloses another preparation of tyramine hydrochloride from p-hydroxyphenyl-α-isonitrosoacetophenone in a reaction medium comprising an aqueous solution without the use of a lower alkyl alcohol.

Pure p-hydroxyphenyl-α-isonitrosoacetophenone (11.7g, 70.9 mmol) and 1.2 g of dry 10% palladium on carbon were added to a solution containing 18 ml of 37% by volume hydrochloric acid (HCl) and 100 ml of water (the HCl was about 6.7% by weight of the HCl/water solution). The reactor was sealed, then degassed 3 times with nitrogen, then 3 times with hydrogen. The reactor was then pressurized to about 50 psi with hydrogen, with hydrogen being added during the reaction to maintain the about 50 psig. The reaction medium was stirred at about 1200 rpm. The reaction heated itself to 33.4° C., then was heated externally using a heating jacket. The course of the reaction is tabularized below. Again, hydrogen added to the Reactor during the reaction was added from a Surge Vessel, and the decrease in Surge Vessel pressure was an indication of hydrogen consumed.

| Time (min.) | Temp. (°C.) | Reactor Pressure (psig.) | Surge Vessel (psig) |
|---|---|---|---|
| 0 | 25 | 50 | 581 |
| 45 | 32 | 55 | 529 |
| 105 | 63 | 50 | 511 |
| 171 | 55 | 60 | 494 |
| 231 | 58 | 50 | 491 |
| 346 | 61 | 62 | 469 |

This procedure yielded tyramine hydrochloride in 85% yield. The tyramine hydrochloride was isolated by filtering off the catalyst then concentrating the reaction solution in vacuo until crystals formed.

EXAMPLE 3

This example discloses a third preparation of tyramine hydrochloride in a reaction medium which does not contain a lower alkyl alcohol. Water (200 mL) and p-hydroxyisonitrosoacetophenone (18.78 g) were loaded into a 1 liter autoclave along with 2.34 g of dry 10% Pd/C catalyst. The reactor was closed and conditioned with nitrogen then with hydrogen (50 psig) for 10 minutes. The reactor was conditioned again with nitrogen; then the reactor was cooled to 14.7° C. and 37% HCl (40 mL) was suctioned into the vessel. The vessel was again purged and blanketed with hydrogen and the progress of the reaction was as follows:

| Time (min.) | Temp. (°C.) | Reactor Pressure (psig.) | Surge Vessel (psig) |
|---|---|---|---|
| 0 | 15.8 | 50 | 428 |
| 11 | 34.1 | 50 | 362 |
| 16 | 31.8 | 50 | 354 |
| | Began Heating Reaction | | |
| 52 | 48.3 | 50 | 313 |
| 80 | 51.0 | 50 | 300 |
| 136 | 51.0 | 50 | 291 |
| 161 | 51.0 | 50 | 291 |

The reaction mixture was cooled and filtered, then analyzed. The analysis showed that the reaction had yielded 100% conversion of the p-hydroxyisonitrosoacetophenone, with 93% selectivity to tyramine hydrochloride, and 6% selectivity to octopamine hydrochloride.

EXAMPLE 4

This example discloses the preparation of tyramine hydrochloride from p-hydroxyphenyl-α-isonitrosoacetophenone in a reaction medium comprising an aqueous solution containing a lower alkyl alcohol.

Pure p-hydroxyphenyl-α-isonitrosoacetophenone (100g, 0.54 mmol) and 10g of dry 5% palladium on carbon were added to a solution containing 100 ml of 37% by volume hydrochloric acid (HCl), 100 ml of water, and 300 ml of 90% aqueous ethanol (the HCl was about 9% by weight of the HCl/water/alcohol solution). The reactor was sealed, then degassed 3 times with nitrogen, then 3 times with hydrogen. The reactor was then pressurized to about 100 psig with hydrogen, with hydrogen being added during the reaction to maintain the about 100 psig. The contents of the reactor were agitated at about 1000 rpm. Again, the Surge Vessel pressure decrease was an indication of hydrogen consumed. The reaction heated itself to 42.3° C., then was heated externally using a heating jacket to about 60° C. The course of the reaction is tabularized below.

| Time (min.) | Temp. (°C.) | Reactor Pressure (psig.) | Surge Vessel (psig) |
|---|---|---|---|
| 0 | 28 | 100 | 496 |
| 42 | 37 | 100 | 434 |
| 97 | 42 | 100 | 305 |
| 166 | 37 | 100 | 230 |
| 289 | 37 | 100 | 447 |
| 390 | 58 | 100 | 394 |
| 600 | 58 | 100 | 218 |

This procedure yielded tyramine hydrochloride in 2% yield. The tyramine hydrochloride was isolated by filtering off the catalyst then concentrating the reaction solution in vacuo until crystals formed.

EXAMPLE 5

Preparation of tyramine hydrochloride from p-hydroxyphenyl-α-isonitrosophenone, using reaction conditions very similar to those used by Satzinger et al. The principal distinction here is the use of the p-isomer starting material rather than the m-isomer starting material of Satzinger et al.

Twenty-one and five-tenths grams (21.5 g) of p-hydroxyisonitrosoacetophenone was loaded into a 1 liter autoclave along with 8.0 g of dry 10% Pd/C catalyst. The reactor was closed and conditioned with nitrogen after which a solution containing 200 ml of 70% EtOH(aq) and 33 ml of 37% by volume HCl was suctioned into the vessel. The vessel was conditioned with hydrogen to 14.7 psig, and the progress of the reaction was as follows:

| Time (min.) | Temp. (°C.) | Reactor Pressure (psig.) | Surge Vessel (psig) |
|---|---|---|---|
| 0 | 29 | 14.7 | 534 |
| 7 | 34.5 | 14.7 | 448 |

-continued

| Time (min.) | Temp. (°C.) | Reactor Pressure (psig.) | Surge Vessel (psig) |
|---|---|---|---|
| 28 | 36.7 | 14.7 | 429 |
| 45 | 37 | 14.7 | 414 |
| 65 | 36.4 | 14.7 | 396 |
| 85 | 35.2 | 14.7 | 390 |
| 125 | 32.7 | 14.7 | 383 |
| 150 | 35 | 14.7 | 380 |
| 210 | 31 | 14.7 | 375 |

The reaction product was analyzed after hydrogen consumption was complete and was found to contain a 75% yield of tyramine hydrochloride (17.1 g) and a yield of only 18% octopamine hydrochloride (4.4 g).

EXAMPLE 6

This example discloses the preparation of tyramine hydrochloride from p-hydroxyacetophenone.

The reaction steps involved are shown schematically below:

STEP I

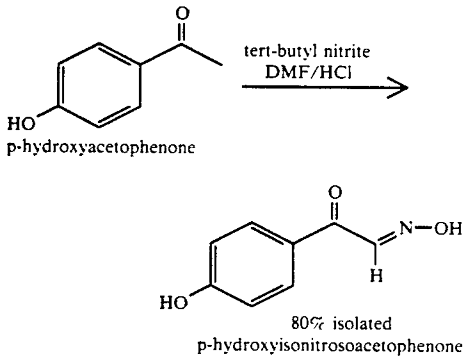

STEP II

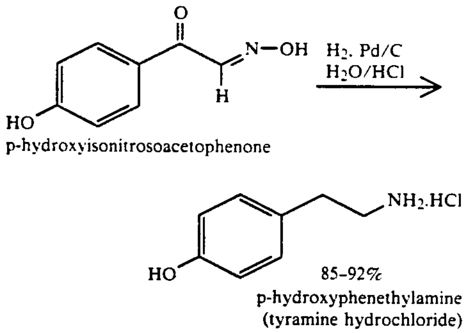

IN STEP I

One thousand (1000) ml of dry dimethyl formamide (DMF) was added to a 3-neck 2 l flask. Subsequently, 2.2 moles of dry HCl were added to the flask. Two hundred seventy-two (272) g (2 moles) of p-hydroxyacetophenone was then added to the flask in a single addition, followed by 296 g (2.2 moles) of 90% tertiary butyl nitrite, which nitrite was added very slowly, over a 2 hour time period, to the flask, to maintain the reaction temperature at about 40° C. After the two hour addition period, the reaction mixture was stirred for an additional 3 hours while the reaction temperature was maintained at about 40°-45° C. using external cooling of the flask. The contents of the flask were then poured over about one liter of ice, from which the reaction product was subsequently extracted using 200 ml of ethylacetate per extraction, and 3 extractions.

The ethylacetate-reaction product organic composition was then concentrated in reaction product by evaporating ethyl acetate under vacuum. The remaining brown oil was poured over about 2 liters of ice. The melted ice-reaction product mixture was then filtered to provide 264 g of p-hydroxyisonitrosoacetophenone, 80% yield based on the p-hydroxyacetophenone.

STEP II

Step II was conducted as described in Example II.

It is to be understood that the above and foregoing Examples are given by way of illustration and that many variations may be made without departing from the spirit and scope of the present invention as encompassed by the following claims.

What is claimed is:

1. A method of preparing the hydrochloride salt of an arylalkylamine, which comprises the steps:

a) providing a compound of the formula

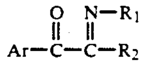

wherein, $R_1$=hydroxyl radical, alkyl, or alkyloxy $R_2$=hydrogen or a $C_1$-$C_8$ alkyl or cycloalkyl, and Ar=an unsubstituted phenyl, or a phenyl substituted only at the ortho position, the para position or both the ortho and para positions, or an unsubstituted naphythyl radical, or a naphthyl radical substituted only at one or more of the 1, 3, 6, and 7 positions, wherein the substituents are selected from the group consisting of amino, alkylamino, dialkylamino, hydroxyl, alkoxy, alkyl, phenyl, benzyl, sulfonic acid, and sulfinic acid radicals, wherein the alkyl component is a branched or unbranched $C_1$-$C_8$ alkyl radical and wherein any of said alkyl, phenyl, and benzyl radicals are optionally substituted with one or more substituents selected from amino, hydroxyl, sulfonic acid, and sulfinic acid radicals, and said phenyl and benzyl substituents are optionally substituted with a $C_1$-$C_8$ alkyl or a $C_1$-$C_8$ alkoxy radical, or both;

b) reacting said compound with hydrogen in an essentially nonalcoholic aqueous reaction medium comprising water, hydrochloric acid, and a hydrogenation catalyst comprising a transition metal on an inert support, wherein sufficient of said catalyst is present in said reaction medium for the amount of said transition metal to range from about 0.0005% by weight to about 1.5% by weight of the initial amount of said compound for which the formula is given above, and wherein said transition metal is selected from the group consisting of platinum, palladium, nickel, rhodium, and combinations thereof; and c) recovering the hydrochloride salt of a compound of the formula Ar-$CH_2CHR_2NH_2$, wherein $R_2$ and Ar are the same as in the compound of step a).

2. The method of claim 1, wherein the step b) moles of hydrogen reacted ranges from about 4 molar equivalents to about 6 molar equivalents, based on the moles of the compound of said formula of step a).

3. The method of claim 2, wherein the reaction is carried out under hydrogen pressure ranging from about 15 psig to about 300 psig, at temperatures ranging from about 5° C. to about 100° C.

4. The method of claim 1, wherein the concentration of the compound of said formula of step a) in said reaction medium is less than about 50% by weight of said reaction medium.

5. A method for the preparation of tyramine hydrochloride, which comprises the steps of:

a) providing p-hydroxy-α-isonitrosoacetophenone;

b) reacting said p-hydroxy-α-isonitroso-acetophenone with hydrogen in an essentially nonalcoholic aqueous reaction medium comprising hydrochloric acid in the presence of a palladium on carbon catalyst, wherein the hydrochloric acid is present in an initial amount ranging from about 2% by weight to about 37% by weight of said reaction medium, and wherein said palladium is present in an amount ranging from about 0.0005% by weight to about 1.5% by weight of the initial amount of said p-hydroxy-α-isonitroso-acetophenone; and c) recovering tryamine hydrochloride from said reaction medium.

6. The method of claim 5, wherein the step b) moles of hydrogen react ranges from about 4 molar equivalents to about 6 molar equivalents, based on one mole of the compound of said formula of step a).

7. The method of claim 6, wherein the reaction is carried out under hydrogen pressure ranging from about 15 psig to about 300 psig, at temperatures ranging from about 5° C. to about 100° C.

8. The method of claim 7, wherein the p-hydroxy-isonitrosoacetophenone is present initially in said reaction medium in an amount ranging from about 5% by weight to about 50% by weight, of said aqueous reaction medium, and wherein said palladium on carbon catalyst is present in said reaction medium at a concentration ranging from about 0.01% by weight to about 10% by weight of said reaction medium.

9. The method of claim 8, wherein said p-hydroxyisonitrosoacetophenone is present initially in said reaction medium in an amount less than about 30% by weight of said reaction medium.

10. A process for the preparation of the hydrochloride salt of an arylalkylamine, which comprises the steps of:

a) providing a compound of the formula

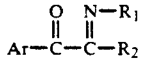

wherein $P_1$ = hydroxyl radical, alkyl, or alkyloxy

R2 = hydrogen or a $C_1$–$C_8$ alkyl or cycloalkyl, and

Ar = an unsubstituted phenyl, or a phenyl substituted only at the ortho position, the para position or both the ortho and para positions, or an unsubstituted naphthyl radical, or a naphthyl radical substituted only at one or more of the 3, 3, 6, and 7 positions, wherein the substituents are selected from the group consisting of amino, alkylamino, dialkylamino, hydroxyl, alkoxy, alkyl, phenyl, benzyl, sulfonic acid, and sulfinic acid radicals, wherein the alkyl components is a branched or unbranched $C_1$–$C_8$ alkyl radical and wherein any of said alkyl, phenyl, and benzyl radicals are optionally substituted with one or more substituents selected from amino, hydroxyl, sulfonic acid, and sulfinic acid radicals, and said phenyl and benzyl substituents are optionally substituted with a $C_1$–$C_8$ alkyl or $C_1$–$C_8$ alkoxy radical, or both;

b) reacting said compound with hydrogen in an aqueous reaction medium which comprises about 90% by weight or less of a lower alkyl alcohol, wherein said aqueous reaction medium also comprises hydrochloric acid present in an initial amount of from about 2% by weight to about 37% by weight of said reaction medium, and a hydrogenation catalyst comprising a transition metal on an inert substrate, wherein sufficient of said catalyst is present in said reaction medium for the amount of said transition metal present to range from about 0.0005% by weight to about 5.0% by weight of the initial amount of said compound for which the formula is given in step a), and wherein said transition metal is selected from the group consisting of platinum, palladium, nickel, rhodium, and combinations thereof; and c) recovering the hydrochloride salt of a compound of the formula $Ar\text{-}CH_2CHR_2NH_2$, wherein $R_2$ and Ar are the same as in the compound of step a).

11. The method of claim 10, wherein the moles of hydrogen reacted in step b) range from about 4 molar equivalents to about 6 molar equivalents based on the moles of said compound of said formula of step a).

12. The method of claim 11, wherein the reaction is carried out under hydrogen pressure ranging from about 15 psig to about 300 psig, at temperatures ranging from about 5° C. to about 100° C.

13. The method of claim 10, wherein said lower alkyl alcohol comprises about 70% by weight or less of said reaction medium.

14. The method of claim 13, wherein said lower alkyl alcohol comprises from about 70% by weight to about by weight of said reaction medium.

15. The method of claim 10, wherein said transition metal, excluding said inert substrate, is present in a quantity ranging from about 0.0005% by weight to about 1.0% by weight, based on the weight of a substituted or unsubstituted aryl-α-oximinoalkyl ketone, as disclosed in the formula of claim 10.

16. The method of claim 10, wherein said hydrogenation catalyst is palladium.

17. The method of claim 16, wherein said palladium, excluding said inert substrate, is present in a quantity ranging from about 0.0005% by weight to about 1.5% by weight based on the weight of a substituted or unsubstituted aryl-α-oximinoalkyl ketone, as disclosed in the formula of claim 10.

18. A method for the preparation of tyramine hydrochloride, which comprises the steps of:

a) providing p-hydroxy-α-isonitrosoacetophenone;

b) reacting said p-hydroxy-α-isonitroso-acetophenone with hydrogen in an aqueous reaction medium which comprises about 90% by weight or less of a lower alkyl alcohol, wherein said reaction medium also comprises hydrochloric acid present in an initial amount of from about 2% by weight to about 37% by weight of said reaction medium, and from about 5% by weight to about 25% by weight of a palladium hydrogenation catalyst comprising palladium on an inert support, wherein said palladium is present in said reaction medium in an amount of from about 0.0005% by weight to about 5.0% by weight of the initial amount of said p-hydroxy-α-isonitrosoacetophenone; and c) recovering tyramine hydrochloride from said reaction medium.

19. The method of claim 18, wherein the hydrogen reacted in step b) ranges from about 4 molar equivalents to about 6 molar equivalents based on the moles of the compound of formula of step a).

20. The method of claim 19, wherein said reaction is carried out under hydrogen pressure ranging from about 15 psig to about 300 psig, at temperatures ranging from about 5° C. to about 100° C.

21. The method of claim 20, wherein said lower alkyl alcohol comprises about 70% by weight or less of said reaction medium.

22. The method of claim 18, wherein said lower alkyl alcohol is selected from the group consisting of $CH_3oH$, ethanol, isopropanol, tertiarybutanol, or $C_1$–$C_8$ cyclic or acyclic alcohols.

23. A method of preparing a salt of a substituted or unsubstituted arylalkylamine from an arylalkylketone, comprising the steps:

a) providing an arylalkylketone of the formula

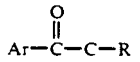

wherein,

R=represents hydrogen, a $C_1$–$C_8$ alkyl or cycloalkyl, and

Ar=represents an aromatic phenyl radical which is unsubstituted, substituted only at the ortho position, substituted only at the para position, or substituted only at both the ortho and para positions, or Ar=represents a naphthyl radical which is unsubstituted, or substituted only at one or more of the 1, 3, 6, and 7 positions, where the substituent is selected from the group consisting of amino, alkylamino, dialkylamino, hydroxyl, alkoxy, alkyl, phenyl, benzyl, aryloxy, sulfonic acid, and sulfinic acid radicals, wherein the alkyl in the alkyl-containing substituent is a branched or unbranched $C_1$–$C_8$ alkyl radical and wherein said alkyl radical as well as said phenyl and benzyl radicals may be optionally substituted with one or more substituents selected from amino, hydroxyl, sulfonic acid, and sulfinic acid radicals, said phenyl and benzyl substituents also or alternatively being optionally substituted with one or more $C_1$–$C_8$ alkyl or $C_1$–$C_8$ alkoxy, or both radicals;

b) reacting said arylalkylketone with a lower alkyl nitrite in the presence of hydrogen chloride and in the presence of a dipolar aprotic solvent to produce a reaction mixture which includes an aryl-alphaoximinoalkylketone reaction product;

c) removing protic by-products of the dipolar aprotic solvent of step b) when such protic by-product is capable of interfering with a hydrogenation catalyst used in step d) below;

d) reacting the aryl-alpha-oximinoalkylketone of step b) with hydrogen in an essentially nonalcoholic aqueous reaction medium comprising water, hydrochloric acid present in an initial amount of from about 2% by weight to about 37% by weight of said reaction medium, and a hydrogenation catalyst comprising a transition metal on an inert support, wherein sufficient of said catalyst is present in said reaction medium for the amount of said transition metal to range from about 0.0005% by weight to about 1.5% by weight of the initial amount of said compound for which the formula is given above, and wherein said transition metal is selected from the group consisting of platinum, palladium, nickel, rhodium, and combinations thereof; and e) recovering the hydrochloride salt of a compound of the formula Ar-$CH_2CHR_2NH_2$, wherein $R_2$ and Ar are the same as in the compound of step a).

24. The method of claim 23, wherein the hydrogen reacted in step d) ranges from about 4 molar equivalents to about 6 molar equivalents, based on the moles of said aryl-α-oximinoalkyl of step b).

25. A method of preparing a salt of a substituted or unsubstituted amine from an arylalkylketone comprising the steps of:

a) providing an arylalkylketone of the formula

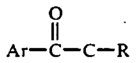

wherein,

R represents hydrogen, a $C_1$–$C_8$ alkyl or cycloalkyl, and

Ar represents an aromatic phenyl radical which is unsubstituted, substituted only at the ortho position, substituted only at the para position, or substituted only at both the ortho and para positions, or Ar represents a naphthyl radical which is unsubstituted, or substituted only at one or more of the 1, 3, 6 and 7 positions, where the substituent is selected from the group consisting of amino, alkylamino, dialkylamino, hydroxyl, alkoxy, alkyl, phenyl, benzyl, aryloxy, sulfonic acid, and sulfinic acid radicals, wherein the alkyl in the alkyl-containing substituent is a branched or unbranched $C_1$–$C_8$ alkyl radical and wherein said alkyl radical as well as said phenyl and benzyl radicals may be optionally substituted with one or more substituents selected from amino, hydroxyl, sulfonic acid, and sulfinic acid radicals, said phenyl and benzyl substituents also or alternatively being optionally substituted with one or more $C_1$–$C_8$ alkyl or $C_1$–$C_8$ alkoxy, or both radicals;

b) reacting said arylakylketone with a lower alkyl nitrite in the presence of hydrogen chloride and in the presence of a dipolar aprotic solvent to produce a reaction mixture which includes an aryl-alphaoximinoalkylketone reaction product;

c) removing protic by-products of the dipolar aprotic solvent of step b) when such protic by-product is capable of interfering with a hydrogen catalyst used in step d) below;

d) reacting the aryl-alpha-oximinoalkylketone of step b) with hydrogen in an aqueous reaction medium which comprises about 90% by weight or less of a lower alkyl alcohol, wherein said aqueous reaction medium also comprises hydrochloric acid present in an initial amount of from about 2% by weight to about 37% by weight of said reaction medium, and a hydrogenation catalyst comprising a transition metal on an inert substrate, wherein sufficient of said catalyst is present in said reaction medium for the amount of said transition metal present to range from about 0.0005% by weight to about 5.0% by weight of the initial amount of said compound for which the formula is given in step a), and wherein said transition metal is selected from the group consisting of platinum, palladium, nickel, rhodium, and combinations thereof; and e) recovering the hydrochloride salt of a compound of the formula Ar-$CH_2CHR_2NH_2$, wherein $R_2$ and Ar are the same as in the compound of step a).

26. The method of claim 25, wherein the moles of hydrogen reacted in step d) ranges from about 4 molar equivalents to about 6 molar equivalent, based on the moles of said aryl-α-oximinoalkyl of step b).

27. A method of preparing the hydrochloride salt of an arylalkylamine, which comprises the steps:

a) providing a compound of the formula

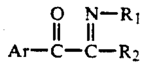

wherein, $R_1$=hydroxyl radical, alkyl, or alkyloxy $R_2$=hydrogen or a $C_1$-$C_8$ alkyl or cycloalkyl, and Ar=an unsubstituted phenyl, or a phenyl substituted only at the ortho position, the para position or both the ortho and para positions, or an unsubstituted naphthyl radical, or a naphthyl radical substituted only at one or more of the 1, 3, 6, and 7 positions, wherein the substituents are selected from the group consisting of amino, alkylamino, dialkylamino, hydroxyl, alkoxy, alkyl, phenyl, benzyl, sulfonic acid, and sulfinic acid radicals, wherein the alkyl component is a branched or unbranched $C_1$-14 $C_8$ alkyl radical and wherein any of said alkyl, phenyl, and benzyl radicals are optionally substituted with one or more substituents selected from amino, hydroxyl, sulfonic acid, and sulfinic acid radicals, and said phenyl and benzyl substituents are optionally substituted with a $C_1$-$C_8$ alkyl or a $C_1$-$C_8$ alkoxy radical, or both;

b) reacting said compound with hydrogen in an aqueous reaction medium comprising hydrochloric acid present in an initial minor weight percent of said reaction medium and a hydrogenation catalyst comprising a transition metal of an inert support, wherein said transition metal is selected from the group consisting of platinum, palladium, nickel, rhodium, and combinations thereof; and c) recovering the hydrochloride salt of a compound of the formula Ar-$CH_2CHR_2NH_2$, wherein $R_2$ and Ar are the same as in the compound of step a).

28. The method of claim 27 in which said compound of step a) is initially present in step b) in an amount equal to from about 5% to about 50% of the weight of said reaction medium.

29. The method of claim 28 in which sufficient of said catalyst is present in said reaction medium for the amount of said transition metal to range from about 0.0005% by weight to about 5.0% by weight of the initial amount of said compound for which the formula is given above.

30. The method of claim 29 wherein said hydrochloric acid is present in said reaction medium in an initial amount of from about 2% to about 37% by weight of said medium.

31. The method of claim 30 in which the reaction is carried out under a hydrogen pressure of from about 15 psig to about 300 psig and at temperature of from about 5° C. to about 100° C.

32. The method of claim 31 in which the reaction is carried out under a hydrogen pressure of from about 45 to about 100 psig.

33. The method of claim 1 in which the amount of compound of step a) is in a range from about 5% to about 50% on the weight of the reaction medium.

34. The method of claim 33 in which said hydrochloric acid is present in an initial amount of from about 2% by weight to about 37% by weight of said reaction medium.

35. The method of claim 34 in which the ratio of catalyst transition metal to hydrochloric acid is from about 0.01 w% to about 37.5 w%.

36. The method of claim 35 in which the ratio of catalyst transition metal to hydrochloric acid extends from 0.01 w% where (i) the amount of said compound of step a) is at the maximum of said range therefor equal to 50% of the weight of the reaction medium, (ii) said ratio of said catalyst transition metal to said compound of step a) is at the minimum of said range therefor equal to 0.0005 w%, and (iii) said acid is at the minimum of said range therefor equal to 2 w% of said reaction medium, to 0.20 w% where (iv) the amount of said compound of step a) is at the minimum of said range therefor equal to 5% of the weight of the reaction medium, (v) said ratio of said catalyst transition metal to said compound of step a) is at the maximum of said range therefor equal to 1.5 w% of said reaction medium, and (vi) said acid is at the maximum of said range therefor equal to 37 w% of said reaction medium.

37. The method of claim 35 in which the transition metal is palladium, the weight of said compound reacted in said reaction medium initially is equal to from about 5% to 15% on the weight of said reaction medium, the ratio of palladium to said compound is from about 0.001 w% to about 1.5 w%, and the ratio of palladium to hydrochloric acid initially present in said reaction medium is less than 4.0 w%.

38. The method of claim 34 in which the reaction is carried out at a hydrogen pressure of from about 45 psig to about 100 psig.

39. The method of claim 9 in which the weight of said p-hydroxy-α-isonitrosoacetophenone reacted in said reaction medium initially is equal to about from 5% to 15% of the weight of said reaction medium, the ratio of palladium to said p-hydroxy-α-isonitrosoacetophenone is from about 0.001 w% to about 1.5 w%, and the ratio of palladium to hydrochloric acid initially present is less than about 4.0 w%.

* * * * *